(12) United States Patent
Wiesinger et al.

(10) Patent No.: US 12,376,759 B2
(45) Date of Patent: Aug. 5, 2025

(54) SYSTEM AND METHOD FOR IMPROVING MAGNETIC RESONANCE SCANNING WORKFLOW

(71) Applicant: GE Precision Healthcare LLC, Wauwatosa, WI (US)

(72) Inventors: Florian Wiesinger, Freising (DE); Dattesh Dayanand Shanbhag, Bengaluru (IN); Kavitha Manickam, Pewaukee, WI (US); Harsh Kumar Agarwal, Jaipur (IN); Dawei Gui, Sussex, WI (US); Chitresh Bhushan, Schenectady, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 394 days.

(21) Appl. No.: 18/090,131

(22) Filed: Dec. 28, 2022

(65) Prior Publication Data

US 2024/0215848 A1 Jul. 4, 2024

(51) Int. Cl.
*G06K 9/00* (2022.01)
*A61B 5/055* (2006.01)
*G01R 33/58* (2006.01)
*G01R 33/54* (2006.01)

(52) U.S. Cl.
CPC ............. *A61B 5/055* (2013.01); *G01R 33/58* (2013.01); *G01R 33/543* (2013.01)

(58) Field of Classification Search
CPC .... A61B 5/055; G01R 33/288; G01R 33/543; G01R 33/58
See application file for complete search history.

(56) References Cited

U.S. PATENT DOCUMENTS 9,547,057 B2 * 1/2017 Rearick ................. G01R 33/48
10,088,539 B2 * 10/2018 Wiesinger .......... G01R 33/4826
10,514,431 B2 12/2019 Liu
(Continued)

FOREIGN PATENT DOCUMENTS

IN 202241043290 10/2022

OTHER PUBLICATIONS

Hennel et al., ""Silent" MRI With Soft Gradient Pulses," Magnetic Resonance in Medicine, 1999, Wiley Online Library, vol. 6, 5 pgs.
(Continued)

*Primary Examiner* — Avinash Yentrapati
(74) *Attorney, Agent, or Firm* — Fletcher Yoder, P.C.

(57) ABSTRACT

A method for performing a scan of a subject utilizing a magnetic resonance imaging (MRI) system includes triggering a prescan by an MRI scanner of the MRI system upon the subject being setup on a table of the MRI scanner and the table reaching an iso-center of the MRI scanner. The method includes subsequent to the prescan, triggering a calibration scan of the subject with the MRI scanner, wherein the calibration scan is an acoustic noise suppressed MRI scan. The method includes obtaining calibration data from the calibration scan. The method includes obtaining prescription parameters for subsequent scans of the subject with the MRI scanner from the calibration data. The method includes triggering at least one scan of the subject with the MRI scanner based on the prescription parameters.

20 Claims, 7 Drawing Sheets

(56) References Cited

U.S. PATENT DOCUMENTS

| | | | |
|---|---|---|---|
| 11,506,739 B2 | 11/2022 | Gui et al. | |
| 11,906,607 B2* | 2/2024 | Eggers | G01R 33/56518 |
| 2016/0069970 A1* | 3/2016 | Rearick | G01R 33/3856 |
| | | | 324/309 |
| 2017/0003364 A1* | 1/2017 | Harvey | G01R 33/4816 |
| 2017/0035301 A1* | 2/2017 | Lechner-Greite | A61B 5/7285 |
| 2017/0261577 A1* | 9/2017 | Smink | G01R 33/4816 |
| 2018/0143272 A1* | 5/2018 | Liu | G01R 33/36 |
| 2021/0080531 A1 | 3/2021 | Gui et al. | |
| 2021/0177295 A1 | 6/2021 | Maximo et al. | |
| 2021/0231761 A1* | 7/2021 | Eggers | G01R 33/4828 |
| 2023/0042314 A1* | 2/2023 | Shih | G01R 33/48 |
| 2024/0118356 A1* | 4/2024 | Zhao | A61B 5/055 |

OTHER PUBLICATIONS

Ljungberg et al., "Silent Zero TE MR Neuroimaging: Current State-of-the-Art and Future Directions," Progress in Nuclear Magnetic Resonance Spectroscopy, Elsevier, 2021, 21 pgs.

Srinivas et al., "External Dynamic InTerference Estimation and Removal (EDITER) for Low Field MRI," Magnetic Resonance In Medicine, 2021, 32 pgs.

U.S. Appl. No. 17/973,855, filed Oct. 26, 2022, Shanbhag.

\* cited by examiner

SYSTEM AND METHOD FOR IMPROVING MAGNETIC RESONANCE SCANNING WORKFLOW

BACKGROUND

The subject matter disclosed herein relates to medical imaging and, more particularly, to an improved scanning workflow for a magnetic resonance imaging (MRI) system.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During MRI, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, Mt. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

In MRI scanning, many concepts have been developed to address workflow automation. These concepts such as intelligent localizer, an autostart feature, or intelligent prescription are based on calibration scans and intelligent protocoling. However, the problem of getting the correct first scan or patient position within a shorter period is always a challenge in MRI.

For example, an autostart feature (which was introduced in digital video multiplex recorder (DVMR) systems onwards) automatically initiates scanning of the selected protocol upon closure of the scan room door. MR software will trigger the prescan once the door close event is received from firmware. In the autostart feature, the magnet room door (or radio frequency (RF) door) must be closed to start scanning to avoid bidirectional transmission of RF energy outside the imaging or scan room (which can degrade image quality). The autostart feature needs the magnet room door closed and starts the prescan of the localizer when the door is closed. Since the prescan of the localizer starts after the door closure, the technologist cannot gain much time between door closure and walking to the control console. In addition, for the safety of the technologist, scanning only occurs with the magnet door closed to avoid exposing the technologist to prolonged acoustic noise In another example, intelligent prescription (e.g., AIR$_x$™ from General Electric Healthcare) utilizes deep learning algorithms to automatically identify anatomical structures and to prescribe slices for a diagnostic scan. However, the success of intelligent prescription depends on correct localizer images. Getting the correct scan positions for the off-isocenter anatomical scan is always a challenge and requires skilled operators.

In a further example, intelligent localizer tries to solve the problem by getting the center of the localizer from the calibration information available from the prescan. However, the intelligent localizer needs an initial setup of the localizer with an embedded prescan where the localizer scan is adjusted based on the prescan.

There is a lot of dead time between the initial setup of the patient and the arrival of the technologist to the control console. During this time, claustrophobic patients and/or children may experience anxiety or distress. Also, during this time, certain patients may also experience pain or discomfort. This creates psychological stress on the technologist who is trying to conduct the scan as quickly as possible but also correctly.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for performing a scan of a subject utilizing a magnetic resonance imaging (MRI) system is provided. The computer-implemented method includes triggering, via a processor, a prescan by an MRI scanner of the MRI system upon the subject being setup on a table of the MRI scanner and the table reaching an iso-center of the MRI scanner. The computer-implemented method also includes subsequent to the prescan, triggering, via the processor, a calibration scan of the subject with the MRI scanner, wherein the calibration scan is an acoustic noise suppressed MRI scan. The computer-implemented method further includes obtaining, via the processor, calibration data from the calibration scan. The computer-implemented method even further includes obtaining, via the processor, prescription parameters for subsequent scans of the subject with the MRI scanner from the calibration data. The computer-implemented method yet further includes triggering, via the processor, a scan of the subject with the MRI scanner based on the prescription parameters.

In another embodiment, a system for performing a scan of a subject utilizing a MRI system is provided. The system includes a memory encoding processor-executable routines. The system also includes a processor configured to access the memory and to execute the processor-executable routines, wherein the routines, when executed by the processor, cause the processor to perform actions. The actions include triggering a prescan by an MRI scanner of the MRI system upon the subject being setup on a table of the MRI scanner and the table reaching an iso-center of the MRI scanner. The actions also include subsequent to the prescan, triggering a calibration scan of the subject with the MRI scanner, wherein the calibration scan is an acoustic noise suppressed MRI scan. The actions further include obtaining calibration data from the calibration scan. The actions still further include obtaining prescription parameters for subsequent scans of the subject with the MRI scanner from the calibration data. The actions yet further include triggering at least one subsequent scan of the subject with the MRI scanner based on the prescription parameters.

In a further embodiment, a non-transitory computer-readable medium, the computer-readable medium including processor-executable code that when executed by a processor, causes the processor to perform actions. The actions include triggering a prescan by an MRI scanner of an MRI system upon a subject being setup on a table of the MRI scanner and the table reaching an iso-center of the MRI scanner. The actions also include subsequent to the prescan, triggering a calibration scan of the subject with the MRI scanner, wherein the calibration scan is an acoustic noise suppressed MRI scan. The actions further include obtaining calibration data from the calibration scan. The actions still further include obtaining prescription parameters for subsequent scans of the subject with the MRI scanner from the calibration data. The actions yet further include triggering at least one subsequent scan of the subject with the MRI scanner based on the prescription parameters.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

Deep-learning (DL) approaches discussed herein may be based on artificial neural networks, and may therefore encompass one or more of deep neural networks, fully connected networks, convolutional neural networks (CNNs), unrolled neural networks, perceptrons, encoders-decoders, recurrent networks, wavelet filter banks, u-nets, general adversarial networks (GANs), dense neural networks, or other neural network architectures. The neural networks may include shortcuts, activations, batch-normalization layers, and/or other features. These techniques are referred to herein as DL techniques, though this terminology may also be used specifically in reference to the use of deep neural networks, which is a neural network having a plurality of layers.

As discussed herein, DL techniques (which may also be known as deep machine learning, hierarchical learning, or deep structured learning) are a branch of machine learning techniques that employ mathematical representations of data and artificial neural networks for learning and processing such representations. By way of example, DL approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

The present disclosure provides systems and methods for improving an MR scanning workflow. In particular, both a prescan, calibration, and localizer scan are run as separate series before the technologist arrives to the control console (e.g., located in a separate room from the scan room where the MRI scanner is located) and immediately after landmarking. In particular, the disclosed embodiments utilize the dead time between the patient set up and the arrival of the technologist at the control console. This enables the technologist to execute a planned geometry plan (provided to the control console) based on the calibration data and the localizer data for subsequent high-resolution scans (e.g., diagnostic scans) immediately upon reaching the control console. The disclosed embodiments include triggering a prescan by an MRI scanner of the MRI system upon the patient being setup on a table of the MRI scanner and the table reaching an iso-center of the MRI scanner. The disclosed embodiments also include subsequent to the prescan, triggering a calibration scan of the patient with the MRI scanner, wherein the calibration scan is a gradient noise suppressed MRI scan. The disclosed embodiments further include obtaining calibration data from the calibration scan, reconstructing a calibration image from the calibration data, obtaining prescription parameters for subsequent scans of the patient with the MRI scanner from the calibration image, and triggering a localizer scan of the patient with the MRI scanner based on the prescription parameters. These acquisitions automatically start upon receiving a signal indicating that the patient has been setup on the table and the table has reached the iso-center. In addition, the calibration scan may occur irrespective of a status (e.g., open or closed) an RF door of the scan room having the MRI scanner. In particular, the calibration scan may begin while the RF door is still open. In certain embodiments, when needed, RF interference artifacts may be removed from the calibration data and/or localizer data from the localizer scan. The disclosed workflow can be automatically performed with minimal or no extra manual adjustments. The disclosed embodiments reduce the time for the scanning workflow, thus, minimizing the time for the subject of the scan to experience anxiety and/or discomfort. Also, the anxiety and the stress the technologist experiences are reduced. Further, more patients may be scanned over a given time period.

Figure 1:
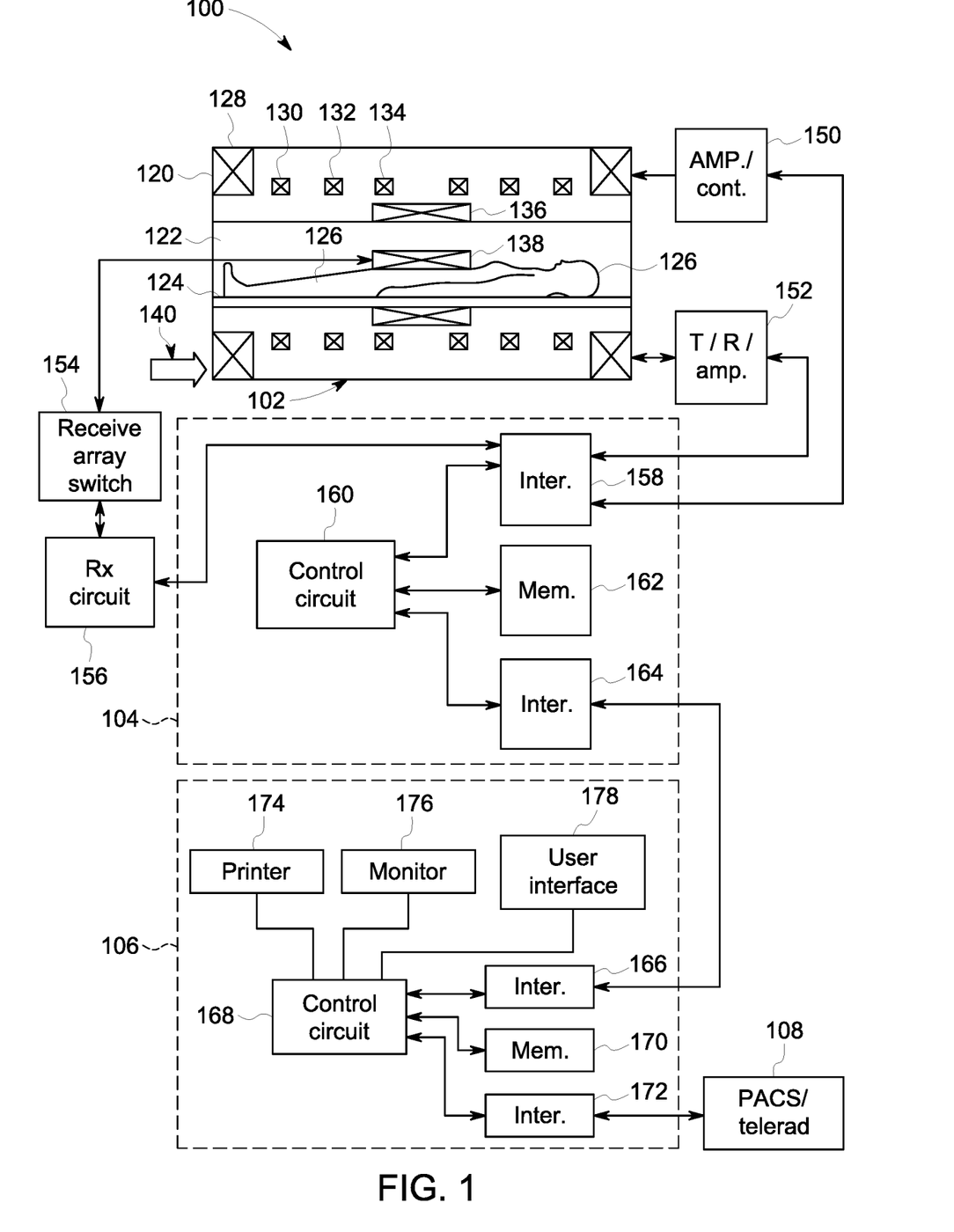
FIG. 1 illustrates an embodiment of a magnetic resonance imaging (MRI) system suitable for use with the disclosed technique.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 (e.g., subject) to be positioned therein for imaging selected anatomy within the patient.

Scanner 102 includes a series of associated coils for producing controlled magnetic fields for exciting the gyromagnetic material within the anatomy of the patient being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, $B_0$. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hardware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data as described below. In certain embodiments, the memory circuit 170 may store one or more neural networks for reconstruction of acquired data as described below. In certain embodiments, image reconstruction may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
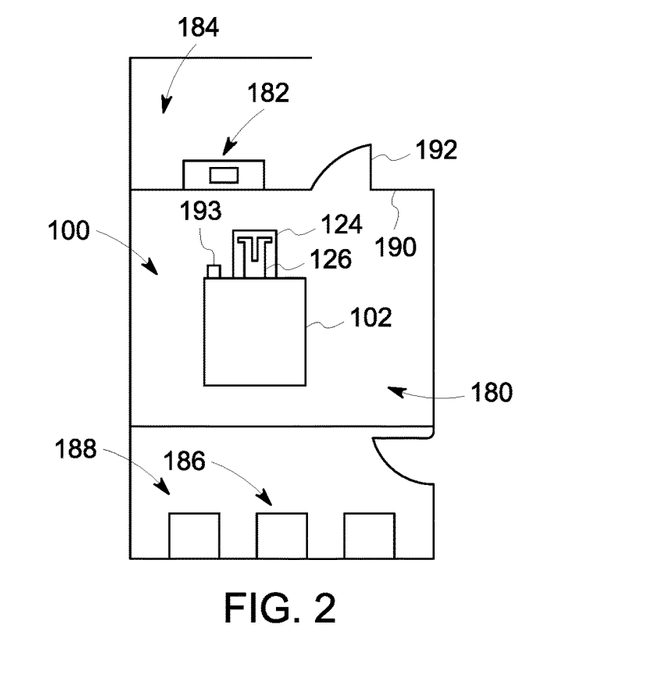
FIG. 2 illustrates an MRI scanner of the MRI system in FIG. 1 disposed in a scan room, in accordance with aspects of the present disclosure.

FIG. 2 illustrates a distribution of the MRI system 100 in a variety of rooms. As depicted, the MRI scanner 102 is located in a scan room or imaging room 180. Components 182 (e.g., user interface 178 in FIG. 1, monitor 176 in FIG. 1, etc.) for controlling the MRI system 100 are disposed in a control room 184 adjacent the scan room 180. Other components 186 (e.g., main power supply 140 in FIG. 1, water pump/chiller, helium pump, gradient and RF cabinets, etc.) may be disposed in a system component room or equipment room 188 adjacent the scan room 180.

Walls 190 of the scan room 180 are constructed in layers and perform several independent functions. For example, the walls 190 include magnetic shielding to confine the fringe field. The walls 190 also include acoustic shielding to restrict noise transmission to the control room 184 and beyond. The walls 190 further include RF shielding to keep electromagnetic noise from entering or leaving the scan room 180. One of the walls 190 includes a door 192 (RF door) that leads to the control room 184. Similar to the walls, the door 192 is also constructed to provide magnetic shielding, acoustic shielding, and RF shielding.

As described in greater detail herein, certain non-diagnostic scans may be conducted (or at least begun) while the door 192 is open. For example, a prescan as well as calibration scans and localizer scans may be conducted (or at least begun) while the door 192 is open. In certain embodiments, a user interface 193 (e.g., button, switch, screen, etc.) may be located on the MRI scanner 102. Once the patient 126 is properly positioned on the table 124 and the table 124 reaches an iso-center of the magnet in the bore 122 of the MRI scanner 102, the technologist (e.g., operator) utilizes the user interface 193 to input or provide a signal (e.g., to control circuitry) to immediately begin in a fully automated manner a sequence of events (e.g., prescan, calibration scan, and localizer scan, etc.). These sequence of events begin regardless of the status of the door 192 (e.g., open or closed). In particular, these sequence of events begin while the door 192 is open. By the time the technologist exits the scan room 180, closes the door 192, and enters the control room 184, a geometry plan for any subsequent scans (e.g., diagnostic scans) has been determined and provided to the technologist at the control console in the control room 184. So all the technologist has to do is to provide the input via the control console to begin the diagnostic scan. This enables the normal dead time to be utilized between patient setup and the first diagnostic scan. This improves the scanning workflow by reducing the time associated with setting up everything before the diagnostic scan. This reduction in time enables more patients to be scanned in a day. In addition, the time for the patient 126 in the MRI scanner 102 is reduced, thus, potentially reducing any anxiety and/or discomfort experienced by the patient 126. Further, the anxiety and stress experienced by the technologist may be reduced.

Figure 3:
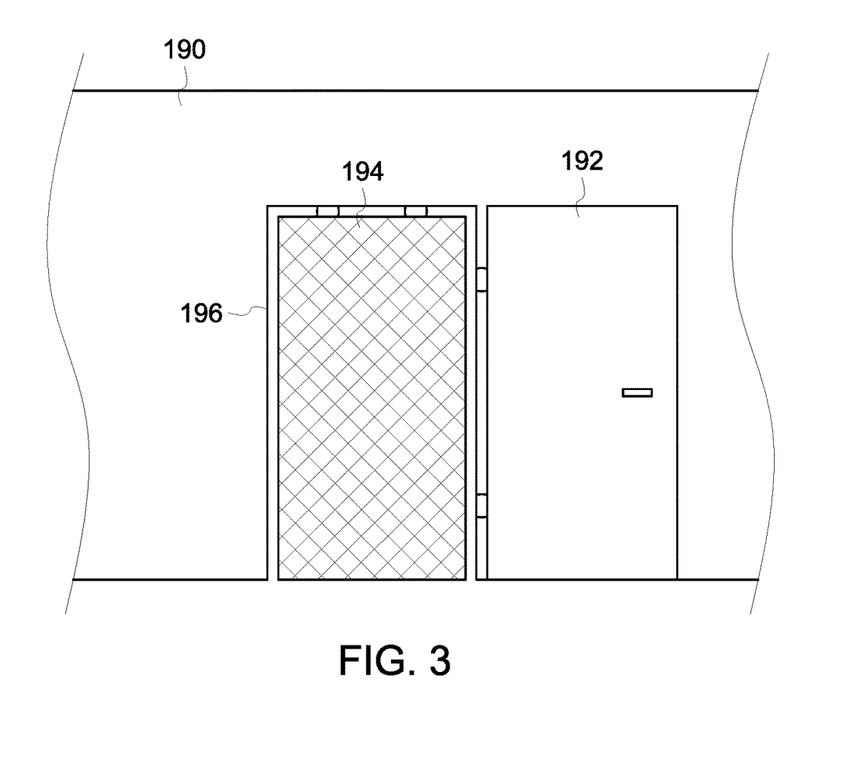
FIG. 3 illustrates a mesh structure or curtain disposed within a door frame of a radio frequency (RF) door, in accordance with aspects of the present disclosure.

Since the door 192 may be open when the sequence of events begins, for the safety of the technologist any scan performed, such as the calibration scan, is performed utilizing an acoustic noise suppressed MRI scan to minimize the acoustic noise from the scan. To keep any RF generated by the MRI scanner 102 from leaking outside the scan room 180 while the door 192 is open, a mesh structure or curtain 194 may be disposed in a door frame 196 of the door 192 as depicted in FIG. 3. The mesh structure or curtain 194 is configured to provide RF shielding to keep RF from leaking into and out of the scan room 180 while the door 192 is open. In certain embodiments, the power sequence utilized by the MRI scanner 102 may be limited to those power sequences with smaller RF amplitudes.

Figure 4:
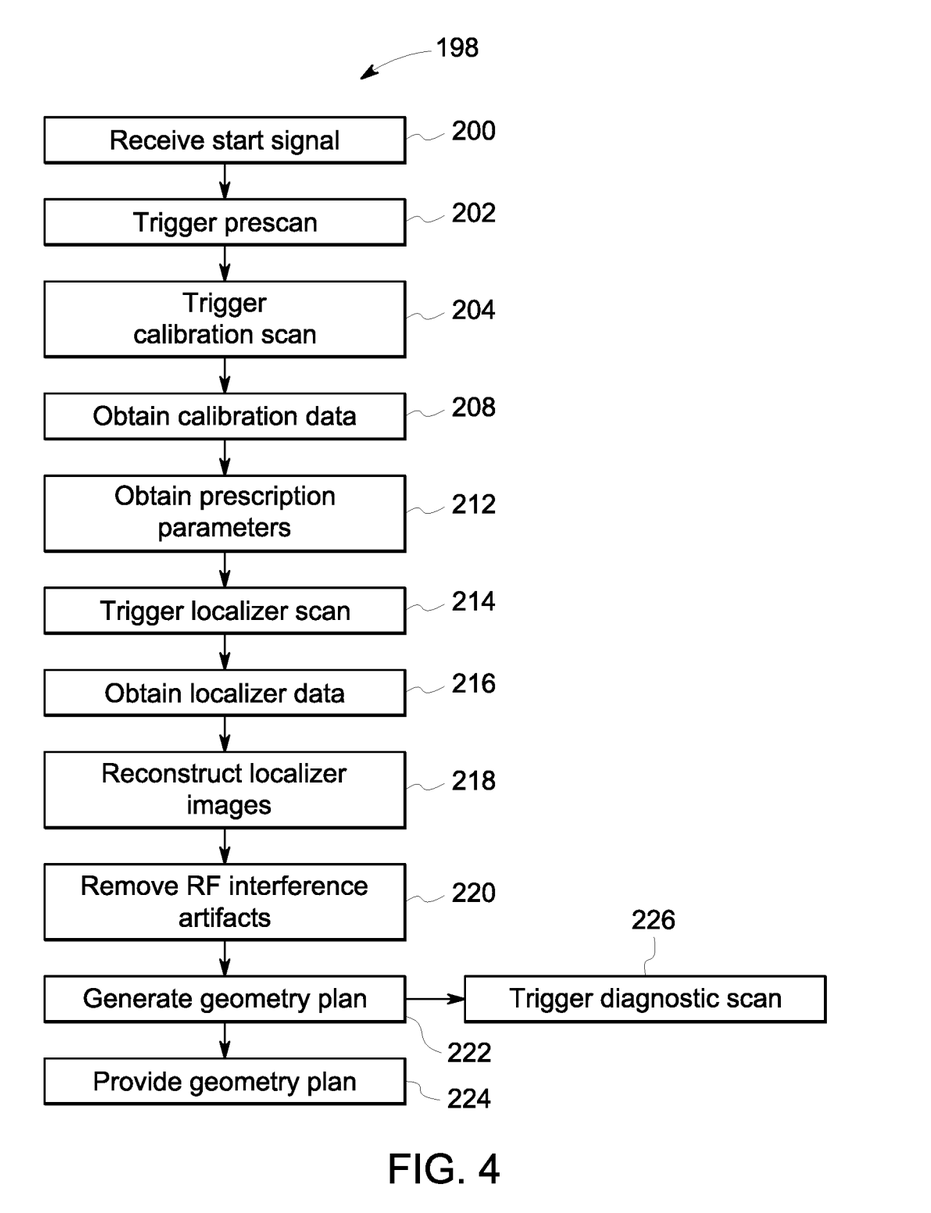
FIG. 4 illustrates a flow diagram of a method for performing a scan of a patient utilizing the MRI system in FIG. 1 utilizing an improved MR scanning workflow, in accordance with aspects of the present disclosure.

FIG. 4 illustrates a flow diagram of a method 198 for performing a scan of a patient utilizing the MRI system 100 in FIG. 1 utilizing an improved MR scanning workflow. One or more steps of the method 198 may be performed by processing circuitry of the magnetic resonance imaging system 100 in FIG. 1. One or more of the steps of the method 198 may be performed simultaneously or in a different order from the order depicted in FIG. 4.

Prior to the start of the method 198, a patient to be imaged is setup by a technologist on a table of the MRI scanner. During the setup, the technologist is ensuring that the patient is properly positioned. Once the patient is properly setup, the table is moved within the bore of the MRI scanner until the patient is iso-center with the magnet in the bore of the MRI scanner. In certain embodiments, in-room cameras or laser-based landmarking may be utilized during this process. The following steps of the method 198 (block 200 to block 226) are fully automated. Once this occurs, the method 198 includes receiving a start signal (e.g., autostart signal) to begin a sequence of events (e.g., prescan, calibration scan, and localizer scan) immediately (block 200). Although the prescan, calibration scan, and the localizer scan are depicted as separate events or scans in the method 198, some or all of these scans may be combined into as few as 1 or 2 three-dimensional scans. The start signal is a user signal input by the technologist by interfacing with a user interface (e.g., screen, button, switch) within the scan room (e.g., coupled to the MRI scanner). Upon providing the start signal, the technologist moves from the scan room to the control room. In certain embodiments, the start signal may be automatically provided (i.e., without user input) upon the table reaching iso-center. The technologist may wear ear protection and/or headphones to reduce exposure to higher noise. In certain embodiments, prior to triggering the prescan, the method 198 includes causing an auditory notification to be provided (e.g., via a speaker) to the patient indicating the beginning of process (e.g., prescan, calibration scan, and subsequent scans). The auditory notification enables the patient to prepare and to let the patient to be still during the process.

The method 198 includes triggering a prescan by the MRI scanner upon receiving the start signal (i.e., upon the patient being setup on a table of the MRI scanner and the table reaching the iso-center of the MRI scanner) (block 202). The prescan may occur or begin irrespective of a status of the RF door (e.g., open or closed). In certain embodiments, the prescan begins and/or occurs while the RF door is open. During the prescan, several calibrations are performed (e.g., to provide tuning values) to ensure optimal performance of specified protocol. A number of steps may occur during the prescan. For example, quick shimming may occur. During quick shimming, small adjustments are made to currents passing through gradients and higher order shim coils to optimize $B_0$ field homogeneity in the presence of the patient. Also, coil tuning and matching may occur. There are differences in the size and the shape of human bodies which crate different loads on the RF coils. Thus, the resonance frequency of the patient coil system needs to be adjusted along with the coil impedance (complex resistance) for effective energy transfer. Further, center frequency adjustment may occur. Human tissues contain both water and fat in various proportions whose resonance peaks differ by a few hundred hertz. The MRI scanner needs to lock on to the correct spectral peak for proper localization. Even further, transmitter attenuation/gain adjustment may occur. The attenuator or amplifier gain of the RF pulse needs to be calibrated for each patient so that the proper flip angle can be obtained. Still further, the receive attenuation/gain adjustment may occur. The MR signal intensity needs to be appropriately scaled so it is neither too big nor too small for the amplifier chain. Yet further, dummy cycles may occur. Dummy cycles are multiple runs of a pulse sequence prior to acquiring data to allow a steady state magnetization to develop.

The method 198 also includes, subsequent to the prescan, triggering a calibration scan (i.e., for a particular protocol) of the patient with the MRI scanner (block 204). In certain embodiments, the calibration scan is part of the prescan and, thus, both the prescan and the calibration are started at the same time. The calibration scan may occur or begin irrespective of a status of the RF door (e.g., open or closed). In certain embodiments, the calibration scan begins and/or occurs while the RF door is open. In certain embodiments, more than one calibration scan may occur. The calibration scan is an acoustic noise suppressed MRI scan to minimize the acoustic noise generated since the RF door may be open still as the technologist moves to the control room. In certain embodiments, the calibration scan may utilize a zero time echo pulse sequence. For example, a Silenz pulse sequence (TE=0, 3D radial center-out k-space filling and data sampling with relatively small gradient steps) may be utilized. In certain embodiments, the calibration scan may utilize a three-dimensional (3D) gradient echo pulse sequence. For example, a Cartesian 3D sequence may be utilized. In certain embodiments, the calibration may utilize any quiet pulse sequence using an acoustic noise reduction technique (ART) based on gradient deration (instead of gradient echo only).

The method 198 also includes obtaining calibration data from the calibration scan (block 208). The method 198 still further includes obtaining prescription parameters for subsequent scans of the patient with the MRI scanner from the calibration data (block 212). In certain embodiments, the prescription parameters are obtained from raw data (k-space data) of the calibration scan. In certain embodiments, the prescription parameters are obtained from a calibration image reconstructed from the calibration data. In certain embodiments, a deep learning-based calibration model or models may be utilized to determine the prescription parameters from the calibration data. In certain embodiments, computer visions techniques may be utilized to determine the prescription parameters from the calibration data. In certain embodiments, statistical learning may be utilized to determine the prescription parameters from the calibration data. In certain embodiments, machine learning may be utilized to determine the prescription parameters from the calibration data. Upon obtaining the prescription parameters, the method 198 includes triggering (e.g., automatically) triggering one or more subsequent scan of the subject with the MRI scanner (e.g., a localizer scan, a high resolution diagnostic scan, etc.).

The method 198 includes triggering a localizer scan (e.g., 3 plane localizer scan) of the patient with the MRI scanner based on the prescription parameters (block 214). In certain embodiments, the localizer scan is fast gradient echo scan. The method 198 also includes obtaining the localizer data from the localizer scan (block 216). The method 198 further includes reconstructing localizer images from the localizer data (block 218). The localizer images are a series of images in the axial, sagittal, and coronal planes. The localizer images enable planning of the slice locations for higher resolution scans (e.g., diagnostic scans) of the patient.

The method 198 further includes removing RF interference artifacts from calibration data (or calibration image) and/or localizer data (or localizer images) obtained during the calibration scan and the localizer scan, respectively (block 220). The removal of the RF interference artifacts may occur as needed. For example, if at least a portion or an entirety of the calibration scan and/or the localizer scan occurred while the RF door was open. In certain embodiments, only the calibration scan may have occurred while the RF door was open. In certain embodiments, both the calibration scan and the localizer scan may have occurred while the RF door was open. In certain embodiments, RF interference removal may occur as a default. The technique utilized for RF interference removal determines when the RF interference removal occurs. In certain embodiments, the RF interference removal may occur in the calibration data before its reconstruction into the calibration image. In certain embodiments, the RF interference removal may occur subsequent to reconstruction on the calibration image. In certain embodiment, the RF interference removal may occur in the localizer data before its reconstruction into the localizer images. In certain embodiments, the RF interference removal may occur subsequent to reconstruction on the localizer images. In certain embodiments, where RF interference was not present RF interference removal is not necessary.

In certain embodiments, RF interference removal may occur utilizing an RF detection coil (e.g., RF sniffer coil) of MRI scanner. The RF detection coil may detect RF noise which may be present during the calibration scan and/or the localizer scan (e.g., due to the RF door being open). The detected RF noise may be utilized to determine a correction or compensation factor to remove RF interference artifacts (or RF noise) from the calibration data and/or localizer data. In certain embodiments, advanced processing techniques or algorithms may be utilized (e.g., the External Dynamic InTerference Estimation and Removal (EDITER)) to remove RF interference artifacts from the calibration data and/or localizer data. In certain embodiments, blocks 200-220 may be repeated by the method 198. For example, the method 198 may include performing an image quality assessment on the obtained data (e.g., calibration data, SAR scout data, localizer data, etc.). In the image quality assessment, a quality metric may be obtained of the data and compared to a desired or predetermined threshold (e.g. of acceptable image quality). If the quality metric falls below the threshold, then the method 198 may immediately repeat blocks 200-220 or wait until the RF door is closed before repeating blocks 200-220.

The method 198 also includes generating a geometry plan for a diagnostic scan based on both the calibration image and the localizer images (block 222). In certain embodiments, deep learning algorithms may be utilized to automatically identify anatomical structures in the calibration image and the localizer images and to prescribe slices for the diagnostic scan. For example, intelligent prescription (e.g., AIR$_x$™ from General Electric Healthcare) may be utilized in generating the geometry plan. In certain embodiments, statistical learning may be utilized to automatically identify anatomical structures in the calibration image and the localizer images and to prescribe slices for the diagnostic scan. In certain embodiments, automatically identify anatomical structures in the calibration image and the localizer images and to prescribe slices for the diagnostic scan.

The method 198 further includes providing the geometry plan (and prescription parameters to the control console (e.g., in the control room) for the technologist (block 224). In certain embodiments, the diagnostic scan of the patient with the MRI scanner is automatically triggered and performed according to the geometry plan (226). In certain embodiments, the automatic trigger of the diagnostic scan may only occur upon receiving a signal (e.g., to firmware) that the RF door is closed. In certain embodiments, the diagnostic scan is not automatically triggered upon generation of the geometry plan.

Figure 5:
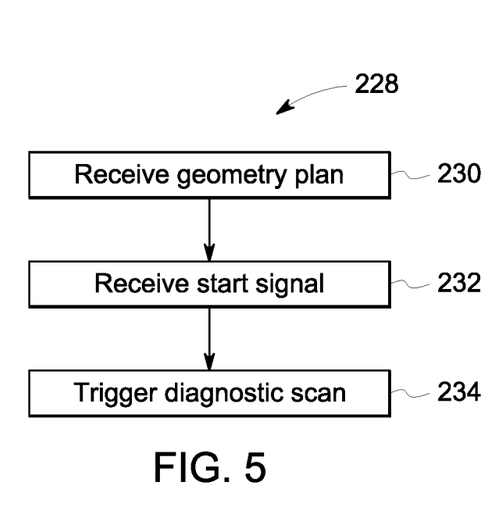
FIG. 5 illustrates a flow diagram of another method for performing a scan of a patient utilizing the MRI system in FIG. 1 utilizing an improved MR scanning workflow, in accordance with aspects of the present disclosure.

FIG. 5 illustrates a flow diagram of another method 228 for performing a scan of a patient utilizing the MRI system 100 in FIG. 1 utilizing an improved MR scanning workflow. One or more steps of the method 228 may be performed by processing circuitry of the magnetic resonance imaging system 100 in FIG. 1. One or more of the steps of the method 228 may be performed simultaneously or in a different order from the order depicted in FIG. 5.

The method 228 includes receiving a geometry plan (and the prescription parameters) at a control console of the MRI system (e.g., in the control room) (block 230). The geometry plan was generated utilizing the method 198 described in FIG. 4. The method 198 in FIG. 4 may occur as the technologist moves from the scan room to the control room. The method 228 also includes receiving a start signal for a diagnostic scan utilizing the MRI scanner (block 232). The start signal is a user signal input by the technologist by interfacing with a user interface (e.g., user interface 178 in FIG. 1) of the control console within the control room. The method 228 further includes triggering the diagnostic scan in response to the start signal (block 234). The diagnostic scan is performed according to the geometry plan.

Figure 6:
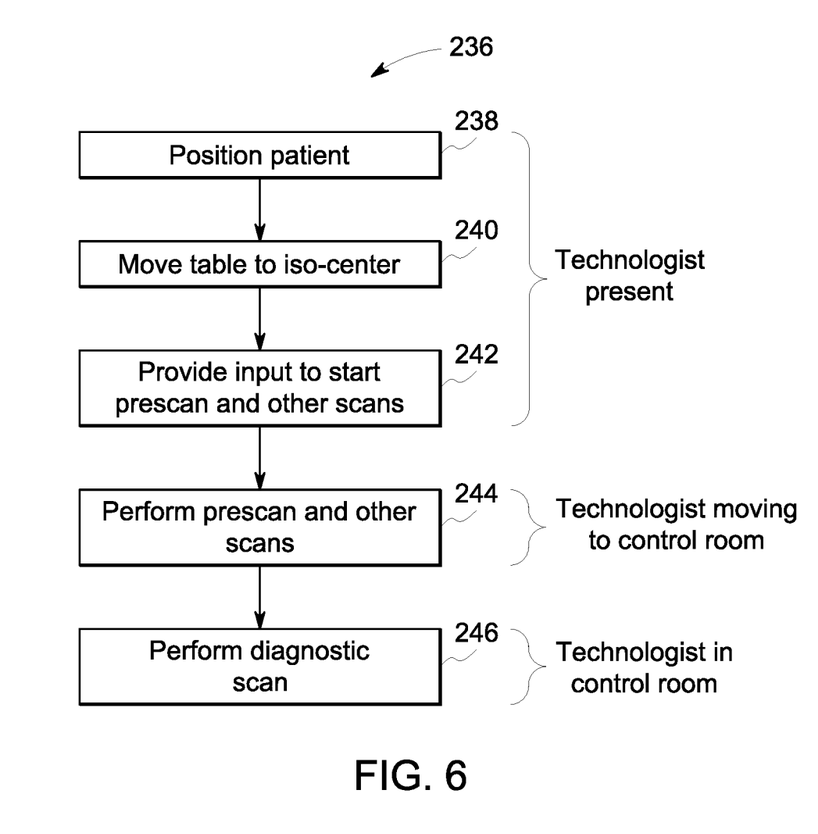
FIG. 6 illustrates a flow diagram of another method for performing a scan of a patient utilizing the MRI system in FIG. 1 utilizing an improved MR scanning workflow, in accordance with aspects of the present disclosure.

FIG. 6 illustrates a flow diagram of another method 236 for performing a scan of a patient utilizing the MRI system 100 in FIG. 1 utilizing an improved MR scanning workflow. The method 236 includes positioning the patient on the table of the MRI scanner (block 238). Once the patient is properly setup, the method 236 includes moving the table within the bore of the MRI scanner until the patient is iso-center with the magnet in the bore of the MRI scanner (block 240). In certain embodiments, in-room cameras or laser-based landmarking may be utilized during this process. Once this occurs, the method 198 includes providing an input to immediately start the sequence of events (e.g., prescan, calibration scan, and localizer scan) as described in the method 198 in FIG. 4 (block 242). The input signal (or start signal) is provided by the technologist by interfacing with a user interface (e.g., screen, button, switch, etc.) within the scan room (e.g., coupled to the MRI scanner). These steps (block 238 to block 242) of the method 242 occur while the technologist or operator is present in the scan room.

Upon providing the start signal, the technologist moves from the scan room to the control room. While the technologist moves between the scan room and the control room, the method 236 includes automatically performing the prescan and other scans (e.g., calibration scan, localizer scan, etc.) as described in the method 198 in FIG. 4 (block 244).

Upon reaching the control room, the geometry plan and associated prescribed parameters are presented to technologist on the control console. The technologist provides an input via a user interface of the control to trigger the performance of the diagnostic scan according to the geometry plan. The method 236 includes performing the diagnostic scan according the geometry plan (block 246).

Figure 7:
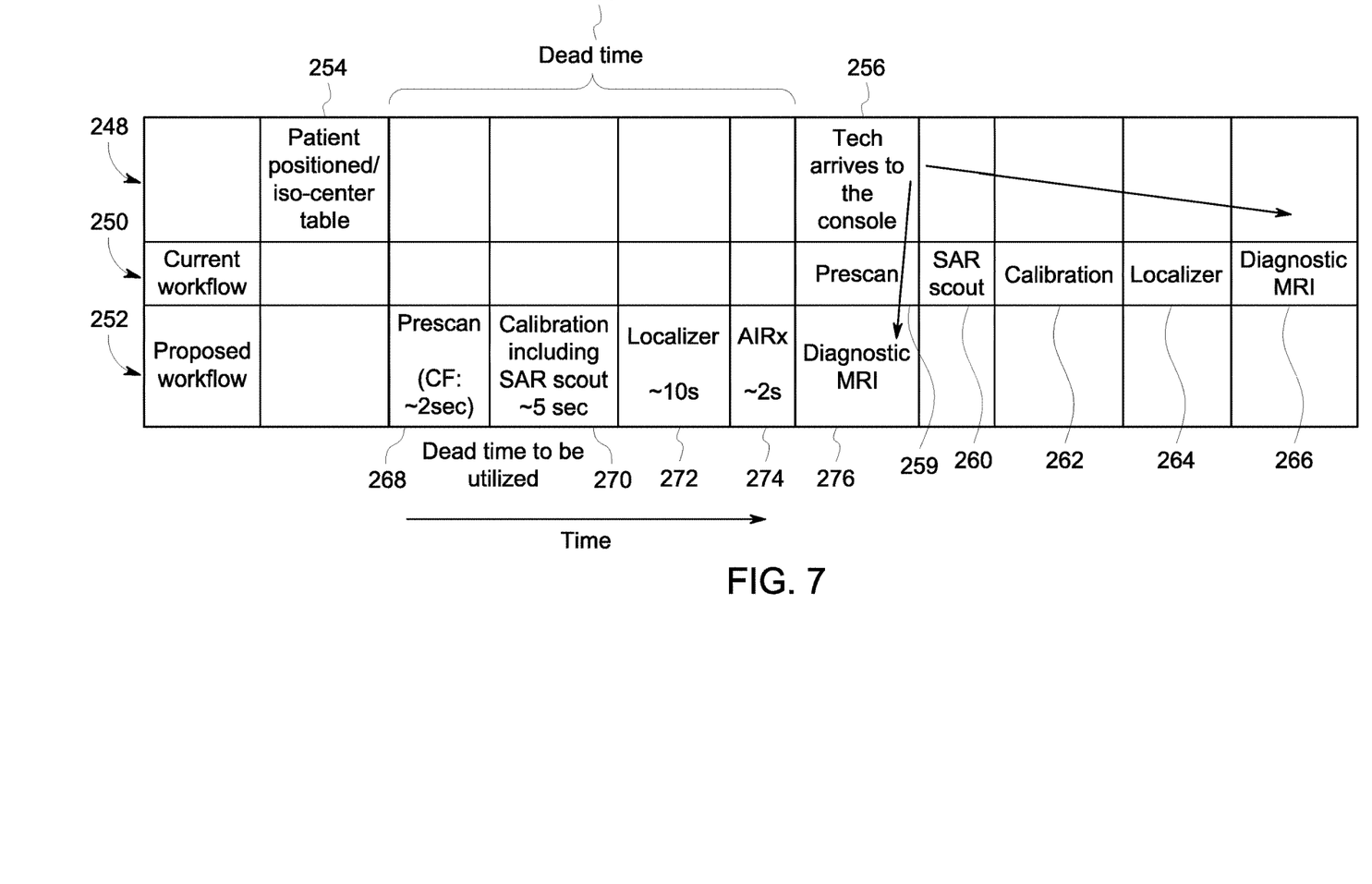
FIG. 7 illustrates a schematic diagram of a comparison of an improved scanning workflow to a current scanning workflow for imaging a patient utilizing the MRI system in FIG. 1, in accordance with aspects of the present disclosure.

FIG. 7 illustrates a schematic diagram of a comparison of an improved scanning workflow (i.e., proposed workflow) to a current scanning workflow for imaging a patient utilizing the MRI system 100 in FIG. 1. A top row 48 illustrates common events over time between the improved scanning workflow and the current scanning workflow. A middle row 250 represents events over time in the current scanning workflow. A bottom row 252 represents events over time in the proposed scanning workflow.

During either of the scanning workflows, the patient is initially positioned and the table of the MRI scanner is iso-centered relative to the magnet of the MRI scanner as represented by reference numeral 254. Once the table is iso-centered, the technologist moves from scan room to the control room where the control console is located as represented by reference numeral 256. In the current workflow, the technologist moving from the scan room to the control room results in dead time (represented by reference numeral 258) where nothing is occurring with regard to scanning.

During this dead time, the patient may be experiencing anxiety and/or discomfort. Also, the technologist may experience some anxiety or stress in trying to complete the scan properly and in a timely manner. In the current workflow, once the technologist reaches the control console in the control room, the technologist begins the prescan as represented by reference numeral 259. Subsequent to the prescan 259, a specific absorption rate (SAR) scout scan (represented by reference numeral 260), a calibration scan (represented by reference numeral 262), and a localizer scan (represented by reference numeral 264) are sequentially performed with the MRI scanner. Upon completing the prescan 259 and the other scans 260, 262, 264, a geometry plan is prescribed and a diagnostic scan (represented by reference numeral 266) is performed according to the geometry plan utilizing the MRI scanner.

Conversely, once the patient is positioned and the table of the MRI scanner iso-centered 254, the improved scanning workflow (upon receiving start signal automatically or from the technologist via a user interface associated with the MRI scanner) automatically performs a sequence of events during the time the technologist moves from the scan room to the control room which would be dead time 258 in the current scanning workflow. The sequence of events includes automatically and sequentially performing a prescan (represented by reference numeral 268), a calibration scan (represented by reference numeral 270), a localizer scan (represented by reference numeral 272), and generation of the geometry plan (e.g., utilizing intelligent prescription such as AIR$_x$™ from General Electric Healthcare) (as represented by reference numeral 274). As depicted, the SAR scout scan may occur during the calibration scan 270. The duration of the events may be approximately 2 seconds, 5 seconds, 10 seconds, and 2 seconds for the prescan 268, the calibration scan 270, the localizer scan 272, and the generation of the geometry plan 274, respectively. In certain embodiments, in the proposed workflow 252, all of these scans 268, 270, and 272 may be permed as a single 3D scan. Once the technologist arrives at the control console, the geometry plan (along with prescribed parameters) are already provided at the control console. The technologist initiates, via the control console, a diagnostic scan (represented by reference numeral 276) that is performed according to the geometry plan utilizing the MRI scanner. In certain embodiments, the diagnostic scan 276 may be performed automatically upon the generation of the geometry plan and the RF door is closed.

In the proposed scanning workflow, the time overall is significantly reduced compared to the current scanning workflow. In particular, the diagnostic scan 276 in the improved scanning workflow is occurring when the prescan is occurring in the current scanning workflow. Thus, a significant amount of time is saved in the improved scanning workflow compared to the current scanning workflow. The improved scanning workflow minimizes the time for the patient to experience anxiety and/or discomfort. Also, the anxiety and the stress the technologist experiences are reduced. Further, more patients may be scanned over a given time period.

Figure 8:
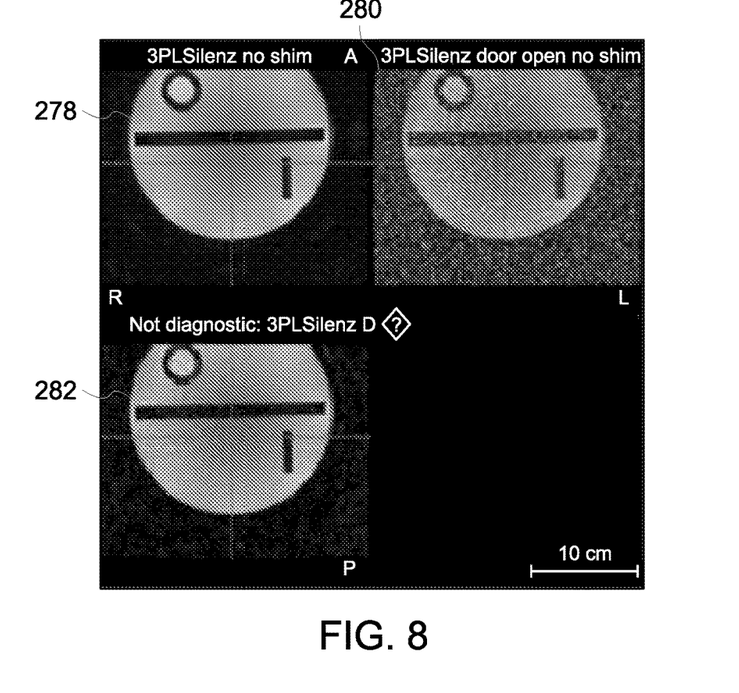
FIG. 8 are axial MRI images of a phantom under different imaging conditions.
Figure 9:
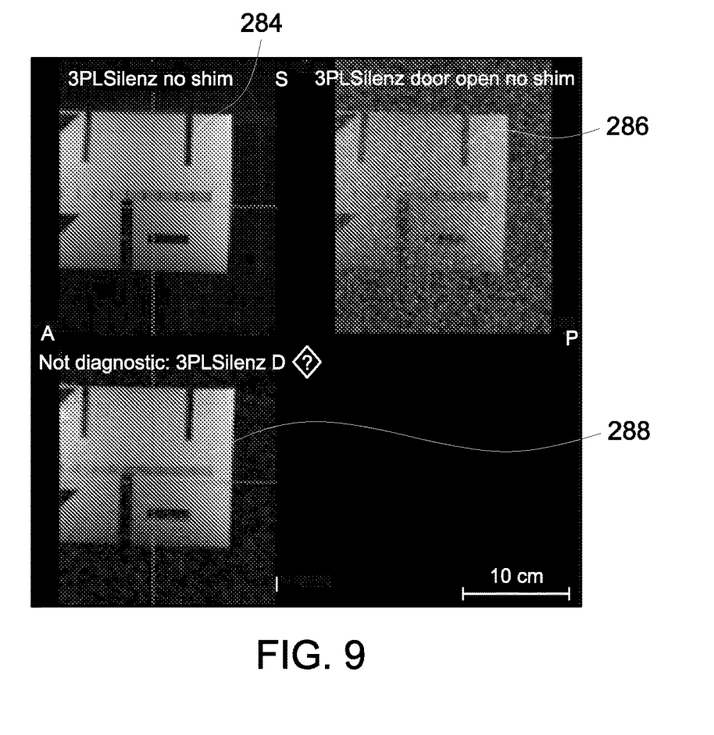
FIG. 9 are sagittal MRI images of the phantom in FIG. 8 under different imaging conditions.
Figure 10:
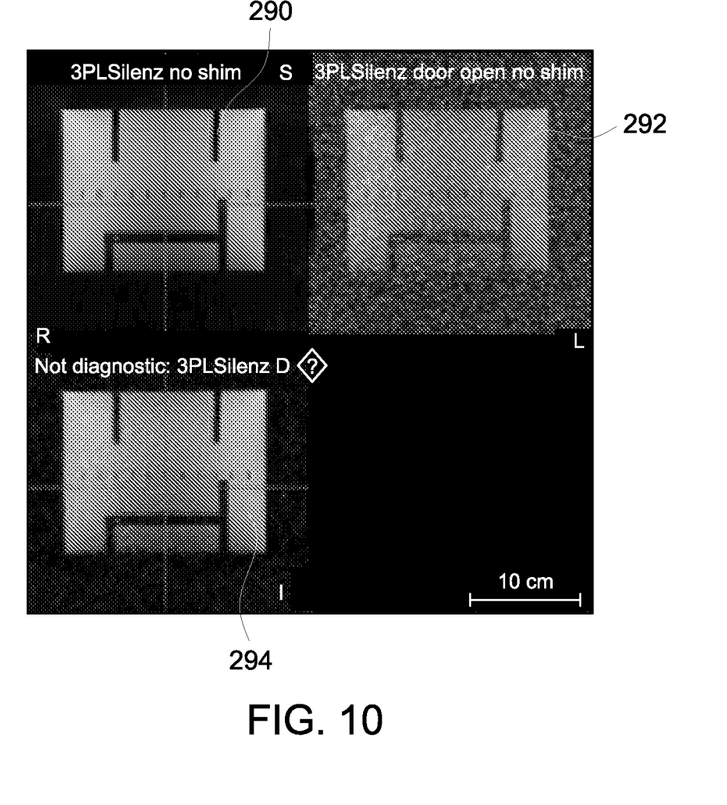
FIG. 10 are coronal MRI images of the phantom in FIG. 8 under different imaging conditions.

FIGS. 8-10 are MRI images of a standard phantom under different imaging conditions. All MRI images were acquired utilizing an 8-channel head (brain) high resolution coil. In addition, the images were acquired utilizing a Silenz pulse sequence to suppress acoustic noise. The MRI images of the phantom in FIG. 8 are along the axial plane. The MRI images of the phantom in FIG. 9 are along the sagittal plane. The MRI images of the phantom in FIG. 10 are along the coronal plane.

MRI image 278 in FIG. 8 was taken with the RF door open. MRI image 280 in FIG. 8 was taken with the RF door open. The RF interference artifacts are visible in MRI image 280 when compared to MRI image 278. MRI image 282 in FIG. 8 was taken with the RF door open utilizing a zero echo time pulse sequence and a deep learning-based reconstruction model. In addition, the RF interference artifacts are removed in MRI image 282 utilizing the techniques described above in FIG. 4. The quality of the MRI image 282 is similar to the quality of the MRI image 278.

MRI image 284 in FIG. 9 was taken with the RF door open. MRI image 288 in FIG. 9 was taken with the RF door open. The RF interference artifacts are visible in MRI image 288 when compared to MRI image 284. MRI image 288 in FIG. 9 was taken with the RF door open utilizing a zero echo time pulse sequence and a deep learning-based reconstruction model. In addition, the RF interference artifacts are removed in MRI image 288 utilizing the techniques described above in FIG. 4. The quality of the MRI image 288 is similar to the quality of the MRI image 284.

MRI image 290 in FIG. 10 was taken with the RF door open. MRI image 292 in FIG. 10 was taken with the RF door open. The RF interference artifacts are visible in MRI image 292 when compared to MRI image 290. MRI image 294 in FIG. 10 was taken with the RF door open utilizing a zero echo time pulse sequence and a deep learning-based reconstruction model. In addition, the RF interference artifacts are removed in MRI image 294 utilizing the techniques described above in FIG. 4. The quality of the MRI image 294 is similar to the quality of the MRI image 290.

Technical effects of the disclosed subject matter include providing an improved scanning workflow for an MRI system. In particular, both a prescan, calibration, and localizer scan are run as separate series before the technologist arrives to the control console (e.g., located in a separate room from the scan room where the MRI scanner is located) and immediately after landmarking. In particular, the disclosed embodiments utilize the dead time between the patient set up and the arrival of the technologist at the control console. This enables the technologist to execute a planned geometry plan (provided to the control console) based on the calibration data and the localizer data for subsequent high-resolution scans (e.g., diagnostic scans) immediately upon reaching the control console. The disclosed improved scanning workflow can be automatically performed with minimal or no extra manual adjustments. The disclosed techniques reduce the time for the scanning workflow, thus, minimizing the time for the subject of the scan to experience anxiety and/or discomfort. Also, the anxiety and the stress the technologist experiences are reduced. Further, more patients may be scanned over a given time period.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for performing a scan of a subject utilizing a magnetic resonance imaging (MRI) system, comprising:
   triggering, via a processor, a prescan by an MRI scanner of the MRI system upon the subject being setup on a table of the MRI scanner and the table reaching an iso-center of the MRI scanner;
   subsequent to the prescan, triggering, via the processor, a calibration scan of the subject with the MRI scanner, wherein the calibration scan is an acoustic noise suppressed MRI scan;
   obtaining, via the processor, calibration data from the calibration scan;
   obtaining, via the processor, prescription parameters for subsequent scans of the subject with the MRI scanner from the calibration data; and
   triggering, via the processor, at least one subsequent scan of the subject with the MRI scanner based on the prescription parameters.

2. The computer-implemented method of claim 1, wherein the acoustic noise suppressed MRI scan utilizes a zero echo time pulse sequence or other quiet pulse sequence using acoustic noise reduction via gradient deration.

3. The computer-implemented method of claim 1, wherein the prescan, and subsequent data acquisition and processing occurs irrespective of whether a radio frequency (RF) door of a scan room where the MRI scanner is located is closed or open.

4. The computer-implemented method of claim 3, wherein the calibration begins to occur while the RF door is open.

5. The computer-implemented method of claim 4, further comprising removing, via the processor, RF interference artifacts from prescan data and/or subsequently acquired data from the at least one subsequent scan.

6. The computer-implemented method of claim 1, wherein obtaining the prescription parameters comprises utilizing a statistical or machine learning based model to obtain the prescription parameters.

7. The computer-implemented method of claim 1, further comprising generating, via a processor, a geometry plan for a diagnostic scan based on both prescan data and the calibration data and a localizer image generated from a localizer scan.

8. The computer-implemented method of claim 7, wherein generating the geometry plan comprises utilizing, via the processor, deep learning algorithms to automatically identify anatomical structures and to prescribe slices for the diagnostic scan.

9. The computer-implemented method of claim 7, further comprising triggering, via the processor, the diagnostic scan based on the geometry plan with the MRI scanner.

10. The computer-implemented method of claim 1, further comprising receiving, via the processor, a start signal to trigger the prescan and consequent scanning.

11. The computer-implemented method of claim 10, wherein the triggering the prescan, triggering the calibration scan, obtaining the calibration data, obtaining the prescription parameters, and triggering the at least one subsequent scan are automatically performed upon receiving the start signal.

12. The computer-implemented method of claim 1, wherein the at least one subsequent scan comprises a localizer scan or a diagnostic scan.

13. The computer-implemented method of claim 1, further comprising performing, via the processor, an assessment of an image quality of the calibration data.

14. The computer-implemented method of claim 1, further comprising, when an image quality of the calibration data is below a predetermined image quality threshold repeating triggering the prescan, triggering the calibration scan, and obtaining the calibration data immediately or upon closing a radio frequency (RF) door of a scan room where the MRI scanner is located.

15. The computer-implemented method of claim 1, further comprising causing, via the processor, an auditory notification to be provided to the subject indicating the prescan and subsequent scanning is about to begin.

16. A system for performing a scan of a subject utilizing a magnetic resonance imaging (MRI) system, comprising:
   a memory encoding processor-executable routines; and
   a processor configured to access the memory and to execute the processor-executable routines, wherein the routines, when executed by the processor, cause the processor to:
      trigger a prescan by an MRI scanner of the MRI system upon the subject being setup on a table of the MRI scanner and the table reaching an iso-center of the MRI scanner;
      subsequent to the prescan, trigger a calibration scan of the subject with the MRI scanner, wherein the calibration scan is an acoustic noise suppressed MRI scan;
      obtain calibration data from the calibration scan;
      obtain prescription parameters for subsequent scans of the subject with the MRI scanner from the calibration data; and
      trigger at least one subsequent scan of the subject with the MRI scanner based on the prescription parameters.

17. The system of claim 16, wherein the acoustic noise suppressed MRI scan utilizes a zero time echo pulse sequence or other quiet pulse sequence using acoustic noise reduction via gradient deration.

18. The system of claim 16, wherein the calibration scan occurs irrespective of whether a radio frequency (RF) door of a scan room where the MRI scanner is located is closed or open.

19. A non-transitory computer-readable medium, the computer-readable medium comprising processor-executable code that when executed by a processor, causes the processor to:
   trigger a prescan by a magnetic resonance imaging (MRI) scanner of an MRI system upon a subject being setup on a table of the MRI scanner and the table reaching an iso-center of the MRI scanner;
   subsequent to the prescan, trigger a calibration scan of the subject with the MRI scanner, wherein the calibration scan is an acoustic noise suppressed MRI scan;

obtain calibration data from the calibration scan;

obtain prescription parameters for subsequent scans of the subject with the MRI scanner from the calibration data; and trigger at least one subsequent scan of the subject with the MRI scanner based on the prescription parameters.

20. The non-transitory computer-readable medium of claim 18, wherein the calibration scan occurs irrespective of whether a radio frequency (RF) door of a scan room where the MRI scanner is located is closed or open.

* * * * *